United States Patent
Lee

(10) Patent No.: US 8,703,224 B2
(45) Date of Patent: Apr. 22, 2014

(54) METHOD TO IMPROVE WATER SOLUBILITY OF REBAUDIOSIDE D

(75) Inventor: Thomas Lee, Scarsdale, NY (US)

(73) Assignee: PepsiCo, Inc., Purchase, NY (US)

( * ) Notice: Subject to any disclaimer, the term of this patent is extended or adjusted under 35 U.S.C. 154(b) by 820 days.

(21) Appl. No.: 12/612,374

(22) Filed: Nov. 4, 2009

(65) Prior Publication Data

US 2011/0104353 A1    May 5, 2011

(51) Int. Cl.
*C07H 15/238* (2006.01)
*A23L 2/60* (2006.01)
*A23L 1/221* (2006.01)

(52) U.S. Cl.
USPC ............................... 426/548; 536/5

(58) Field of Classification Search
None
See application file for complete search history.

(56) References Cited

U.S. PATENT DOCUMENTS

| | | |
|---|---|---|
| 4,361,697 A | 11/1982 | Dobberstein et al. |
| 4,830,862 A | 5/1989 | Braun et al. |
| 4,925,686 A | 5/1990 | Kastin |
| 2007/0292582 A1* | 12/2007 | Prakash et al. ............... 426/548 |
| 2008/0226793 A1 | 9/2008 | Chang et al. |
| 2008/0226802 A1* | 9/2008 | Lee ................................ 426/594 |
| 2011/0092684 A1* | 4/2011 | Abelyan et al. ............... 536/18.1 |

FOREIGN PATENT DOCUMENTS

WO    2008112961 A1    9/2008

OTHER PUBLICATIONS

Shefter, E. et al., Journal of Pharmaceutical Sciences, "Dissolution Behavior of Crystalline Solvated and Nonsolvated Forms of Some Pharmaceuticals", 1963, vol. 52, No. 8, pp. 781-791.*
International Search Report and Written Opinion issued for corresponding PCT/US2010/055237 dated Sep. 15, 2011.

* cited by examiner

*Primary Examiner* — Layla Bland
*Assistant Examiner* — Bahar Craigo
(74) *Attorney, Agent, or Firm* — Banner & Witcoff, Ltd.

(57) ABSTRACT

Thermally stable anhydrous Rebaudioside D can be provided by methods disclosed here and has been found to be more soluble in aqueous solutions than the previously known non-anhydrous Rebaudioside D. This physical property makes the anhydrous Reb D amenable to food and beverage manufacturing applications for which the non-anhydrous form is not suitable. Anhydrous Rebaudioside D is useful in sweeteners, and can be included in food and beverage products, which are also disclosed.

15 Claims, 11 Drawing Sheets

HPLC Chromatogram Analysis Results (UV) for Four Samples of Commercially Available Reb D (hydrate) After Heating in Oven at Four Different Temperatures for Two Hours

HPLC Chromatogram Analysis Results (ELSD and UV) for Commercially Available Reb D (hydrate) Before Undergoing the Heating Process

METHOD TO IMPROVE WATER SOLUBILITY OF REBAUDIOSIDE D

FIELD

Aspects of the disclosure generally relate to a method for improving the water solubility of a steviol glycoside. More specifically, a method is described for improving the water solubility of Rebaudioside D. The method yields a thermally stable anhydrous form of Rebaudioside D suitable for use in traditional processing methods in the food and beverage industry.

BACKGROUND

Steviol glycosides are sweet-tasting compounds extracted from the stevia plant (*Stevia rebaudiana* Bertoni). Typically, these compounds are found to include stevioside, steviolbioside, the Rebaudiosides, including Rebaudioside A (Reb A), Rebaudioside B (Reb B), Rebaudioside C (Reb C), Rebaudioside D (Reb D), and Rebaudioside E (Reb E), and dulcoside A. Many steviol glycosides are potent, non-nutritive sweeteners. Steviol glycosides comprise a diterpene core (formula I) substituted at $R^1$ and $R^2$ with various combinations of hydrogen, glucose, rhamnose, and xylose.

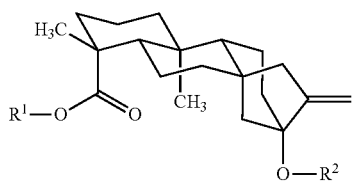

Formula I

For example, $R^1$ may be hydrogen, 1-β-D-glucopyranosyl, or 2-(1-β-glucopyranosyl)-1-β-D-glucopyranosyl, and $R^2$ may be hydrogen, 1-β-D-glucopyranosyl, 2-(1-β-D-glucopyranosyl)-1-β-D-glucopyranosyl, 2,3-bis(1-β-D-glucopyranosyl)-1-β-D-glucopyranosyl, 2-(1-α-L-rhamnopyranosyl)-1-β-D-glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl. Rebaudioside A (wherein $R^1$ is 1-β-D-glucopyranosyl and $R^2$ is 2,3-bis(1-β-D-glucopyranosyl)-1-β-D-glucopyranosyl) has a sweetness of about 200 to 300 times the sweetness of sucrose.

Steviol glycosides are found in the leaves of the stevia plant and each have a particular taste profile and sweetness intensity. Since receiving GRAS status, Reb A has become a popular naturally occurring potent sweetener in the food and beverage industry. Reb A is approximately 200 times sweeter than sucrose, but the sweetness may be offset by problems of off-tastes, for example slow on-set, or bitter, licorice, or lingering aftertaste. Reb D is one of the other sweet steviol glycosides and has a sweetness intensity similar to Reb A, but possesses a more desirable taste profile than many of the other steviol glycosides, including Reb A, Stevioside, Reb C, Reb E, and dulcoside A. Unfortunately, the water solubility of commercially available Reb D is low. This leads to difficulties in making certain Reb D sweetened products, e.g., carbonated beverages, using traditional bottling process methods.

Traditionally, the beverage industry makes certain carbonated beverages by first making concentrated syrup and then diluting the syrup with water at the time and place of making the beverage. The dilution ratio in such beverages is often 1:5, meaning one part syrup is mixed with five parts water. The beverage often is carbonated at the time of being bottled or otherwise packaged. For any ingredient to be incorporated into such a 1:5 syrup, the solubility of the ingredient in the syrup must be at least six times higher than its desired concentration in the finished beverage. Therefore, when comparing the solubility of compounds such as Stevioside (which is found to be only sparingly soluble in water) to Reb A (which contains an additional glucose unit on its structure), Reb A is found to be more soluble than Stevioside. The solubility of Reb A in aqueous solution at room temperature is at least 3000 ppm, enabling the production of a beverage (e.g., carbonated beverage, juice beverage, energy drink, and the like) with a concentration of about 500 ppm of Reb A. In contrast, the stable solubility of Reb D in aqueous solution at room temperature has been found to be no more than about 450 ppm, yielding a beverage containing only about 74 ppm of Reb D. For many beverages, this concentration does not yield a sufficiently effective level of sweet taste to the beverage.

Conventional methods for increasing the solubility of a solid solute in solution include increasing the temperature of the solution. Upon heating Reb D in aqueous solution at temperatures ranging from about 70°-80° C., the solubility of Reb D increases to as much as 0.6%, (6000 ppm), with no apparent decomposition. However, upon cooling the solution to room temperature (e.g., 25° C.), the Reb D precipitates back out of solution within a few hours. The formation of precipitate disrupts and disables the processes utilized in traditional beverage manufacturing.

It is an object of the present disclosure to provide a new, more soluble thermally stable form of Reb D as well as syrups, solutions, beverages, sweeteners, compositions and other products comprising the new soluble thermally stable form of Reb D either alone or with other ingredients. Additional objects, features and advantages will be apparent from the following disclosure and from the discussion of various exemplary embodiments.

BRIEF SUMMARY

The following presents a simplified summary of aspects of the inventive sweeteners, syrups, solutions, beverages, components, products, compositions and methods disclosed here. This summary is not an extensive overview, and it is not intended to identify all or only key or critical elements or to delineate the scope of the inventive sweeteners, syrups, solutions, beverages, components, products, compositions and methods covered by the claims. The following summary merely presents some concepts and aspects of the disclosure in a simplified form as a prelude to the more detailed description provided below of certain exemplary and non-limiting embodiments of the invention.

In accordance with one aspect thermally stable anhydrous Reb D is provided. As used here and in the appended claims, a compound is defined as "thermally stable" when it does not decompose (i.e., does not experience loss of weight as evidenced by spectrometric analysis and/or analytical methods including wet chemistry and other non-spectroscopic analysis techniques) or is otherwise chemically and physically stable upon heating over a high temperature range, e.g., up to 250° C. It is currently understood that such thermally stable anhydrous Reb D is a compound having formula:

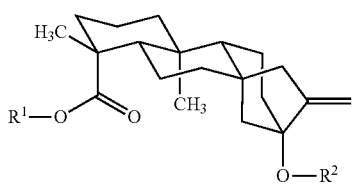

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl.

In accordance with another aspect, a sweetener is provided comprising thermally stable anhydrous Reb D, i.e., an anhydrous compound of formula:

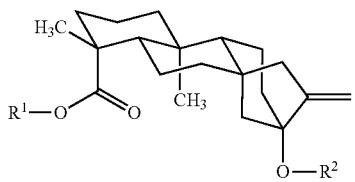

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl.

In accordance with another aspect, a supersaturated aqueous solution is provided of Reb D. A solution is provided that is supersaturated with the compound of formula:

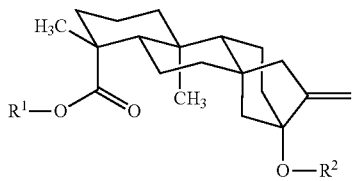

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl. In at least certain exemplary embodiments, such supersaturated aqueous solution has a stable solution of Reb D at a concentration greater than 500 ppm, e.g., 1500 ppm or 3000 ppm. As used here and in the appended claims, a "stable solution" is defined as a solution prepared and stored according to the methods described here where the Reb D remains in solution for a period of time of at least 24 hours at room temperature without forming a precipitate.

In accordance with another aspect, a beverage product is provided comprising:
A) a sweetener component comprising a thermally stable anhydrous compound of formula:

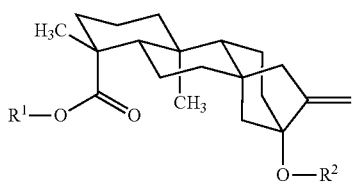

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, and B) at least one other beverage ingredient.

In accordance with other aspects, a beverage product is provided comprising a room temperature aqueous solution comprising a compound of the formula:

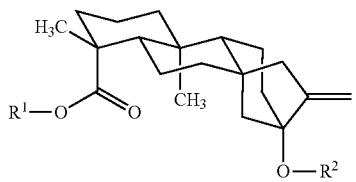

wherein $R^1$ is 2-(1-β-D-glucopyranosyl)-1-β-D-glucopyranosyl and $R^2$ is 2,3-bis(1-β-D-glucopyranosyl)-1β-D-glucopyranosyl, and at least one other beverage ingredient, wherein the compound is at a concentration greater than 500 ppm.

In accordance with other aspects, a beverage product is provided comprising a room temperature aqueous solution comprising a compound of the formula:

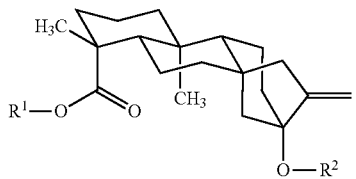

wherein $R^1$ is 2-(1-β-D-glucopyranosyl)-1-β-D-glucopyranosyl and $R^2$ is 2,3-bis(1-β-D-glucopyranosyl)-1β-D-glucopyranosyl, and at least one other beverage ingredient, wherein the compound is at a concentration greater than 3000 ppm.

In accordance with another aspect, a method is provided for preparing a thermally stable anhydrous compound of formula:

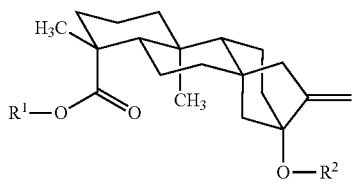

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, comprising heating at least a non-anhydrous form of the compound to a sufficient temperature for a sufficient length of time to convert at least a majority of the non-anhydrous form of the compound to a thermally stable anhydrous form of the compound. In certain exemplary and non-limiting embodiments at least 50% by weight of the non-anhydrous form of the compound is converted to a thermally stable anhydrous form of the compound. In certain exemplary and non-limiting embodiments at least 75% by weight of the non-anhydrous form of the compound is converted to a thermally stable anhydrous form of the compound. In certain exemplary and non-limiting embodiments at least 95% by weight of the non-anhydrous form of the compound is converted to a thermally stable anhydrous form of the compound. In certain exemplary and non-limiting embodiments a non-anhydrous form of the compound is heated at a temperature of at least 80° C., e.g., at a temperature between 80° C. and 110° C., for a period of at least 24 hours, e.g., for a period between 24 hours and 120 hours. In certain exemplary and non-limiting embodiments a non-anhydrous form of the compound is heated under vacuum (i.e., at pressures less than 1 atm) at a temperature of at least 80° C., e.g., at a temperature between 80° C. and 110° C., for a period of at least 24 hours, e.g., for a period between 24 hours and 120 hours.

In accordance with another aspect, a method is provided for preparing a supersaturated aqueous solution comprising the compound of formula:

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, comprising:
A) heating at least a non-anhydrous form of the compound to a temperature of at least 100° C. for a sufficient length of time to convert at least a majority of the non-anhydrous form of the compound to a thermally stable anhydrous form of the compound;
B) dissolving under heat a quantity of the thermally stable anhydrous form of the compound of step A in at least water to form an aqueous solution; and
C) cooling the aqueous solution of step B to room temperature.

In certain exemplary and non-limiting embodiments the aqueous solution of step B is heated to 140° F. (60° C.). In certain exemplary and non-limiting embodiments the aqueous solution in step C cools to room temperature without formation of a precipitate. In certain exemplary and non-limiting embodiments the aqueous solution of step B comprises at least 50% water. In certain exemplary and non-limiting embodiments the concentration of the compound in the aqueous solution of step C is at least 500 ppm and in other embodiments is at least 3000 ppm.

In accordance with another aspect, a method is provided for preparing a sweetened syrup comprising the compound of formula:

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, comprising:
A) heating at least a non-anhydrous form of the compound to a temperature of at least 100° C. for a sufficient length of time to convert at least a majority of the non-anhydrous form of the compound to a thermally stable anhydrous form of the compound;
B) dissolving under heat a quantity of the thermally stable anhydrous form of the compound of step A in at least water to form an aqueous solution;
C) cooling the aqueous solution of step B to room temperature; and
D) adding at least one other food or beverage ingredient.

In accordance with another aspect, a method is provided for preparing a beverage product comprising the compound of formula:

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, comprising:
A) heating at least a non-anhydrous form of the compound to a temperature of at least 100° C. for a sufficient length of time to convert at least a majority of the non-anhydrous form of the compound to a thermally stable anhydrous form of the compound;
B) dissolving under heat a quantity of the thermally stable anhydrous compound of step A in at least water to form an aqueous solution;
C) cooling the aqueous solution of step B to room temperature;
D) adding at least one other beverage ingredient to form a beverage concentrate; and
E) diluting the beverage concentrate of step D with at least water; and
F) optionally adding at least one other beverage ingredient.

In certain exemplary and non-limiting embodiments of such method for preparing a beverage product, the beverage concentrate in step E is diluted in a ratio of 1 part syrup to 5 parts water.

BRIEF DESCRIPTION OF THE DRAWINGS

A more complete understanding of the present disclosure and the advantages thereof may be acquired by referring to the following description in consideration of the accompanying drawings, in which like reference numbers indicate like features, and wherein.

DETAILED DESCRIPTION OF EXEMPLARY EMBODIMENTS

In the following description of the various embodiments, reference is made to the accompanying figures, which form a part hereof, and in which is shown by way of illustration various embodiments in which one or more aspects of the disclosure may be practiced. For convenience, the various embodiments discussed below are sweeteners, syrups, solutions, beverages, components, products, compositions, methods and the like. It is to be understood that other embodiments may be utilized and structural and functional modifications may be made without departing from the scope of the present disclosure.

As illustrated in the figures below, the chemical structure of Reb D is very similar to that of Reb A.

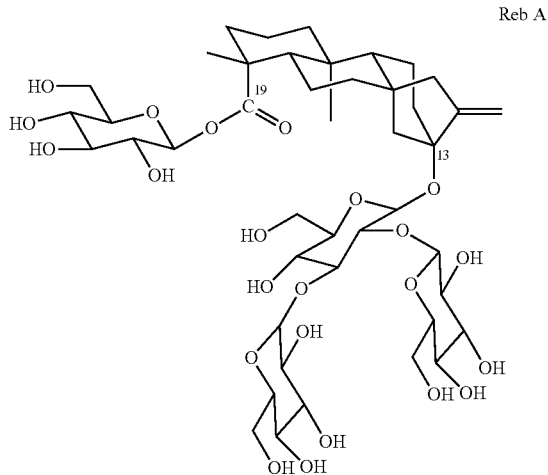

Reb A

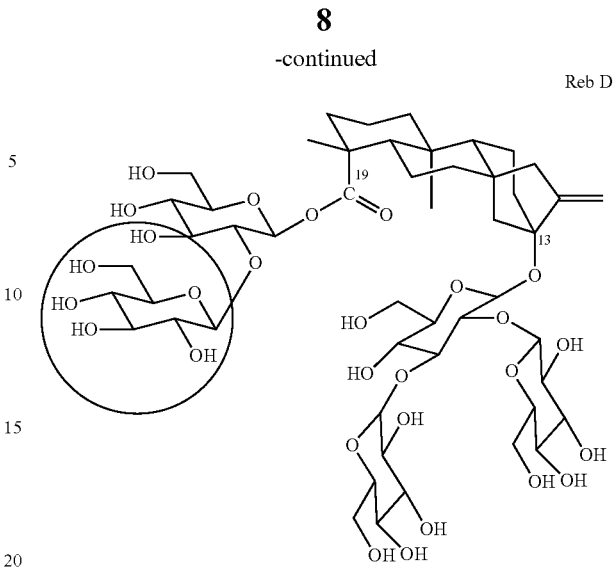

Reb D

The difference between the compounds lies on the C-19 ester moiety. Reb A ester contains one glucose, whereas Reb D has glucosyl-glucose (see circled area in figure above). Traditional solubility theory suggests that adding one more glucose units should increase the water solubility of Reb D, not decrease it.

Without being bound by theory, it is believed that Reb D forms one or more hydrate(s) during its manufacturing process and the hydrate(s) function to inhibit the water solubility of Reb D. Table 1 illustrates elemental analysis that indicates the formation of a tri-hydrate in commercially available Reb D compound.

TABLE 1

| Theoretical Values for Anhydrous Reb D $C_{50}H_{80}O_{28}$ | Found Values | Theoretical Values for Reb D Trihydrate $C_{50}H_{80}O_{28} \cdot 3H_2O$ |
| --- | --- | --- |
| C: 53.19% | C: 50.14%; 50.24% | C: 50.76% |
| H: 7.09% | H: 7.08%; 7.23% | H: 7.28% |
| O: 39.72% | O: 42.13%; 42.32% | O: 41.96% |

Figure 1:
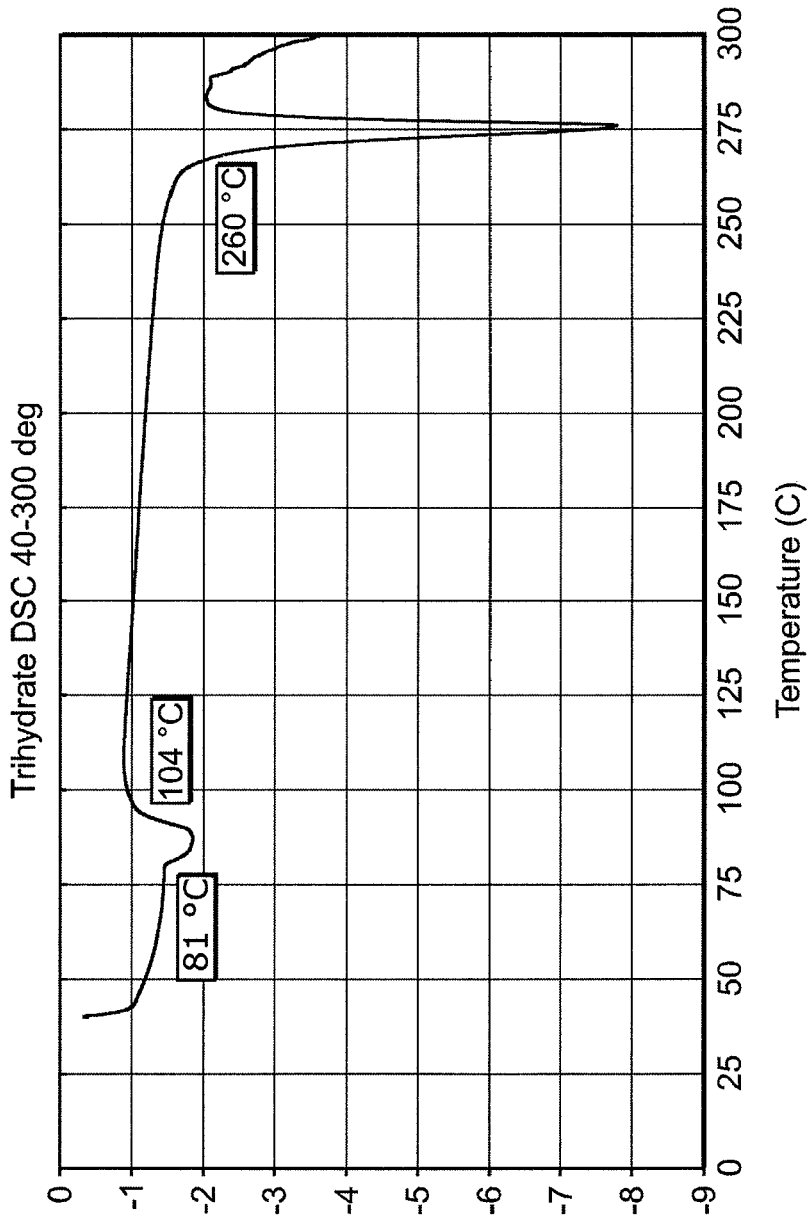
FIG. 1 illustrates a Differential Scanning calorimetry (DSC) thermal energy graph for commercially available Reb D (hydrate).

Differential Scanning calorimetry (DSC) is a test to determine if any phase changes occur as a compound is heated. DSC experiments heat a sample in a controlled environment, and heat gains or losses are measured as a function of temperature. An endothermic heat flow indicates a loss of a volatile compound. As illustrated in FIG. 1, DSC analysis of commercially available Reb D (hydrate) was carried out between 40°-300° C. with heating at 10° C./min. The results indicate a small thermal energy change (an endothermic heat event) between about 81°-104° C. before reaching the melting point above about 260° C. These results indicate a loss of water (or hydrates(s)) in this temperature range. Aside from this small energy change, Reb D appears stable as the heating temperature continues to increase to about 260° C., whereupon apparent decomposition occurred, as evidenced by a large endothermic event.

Figure 2:
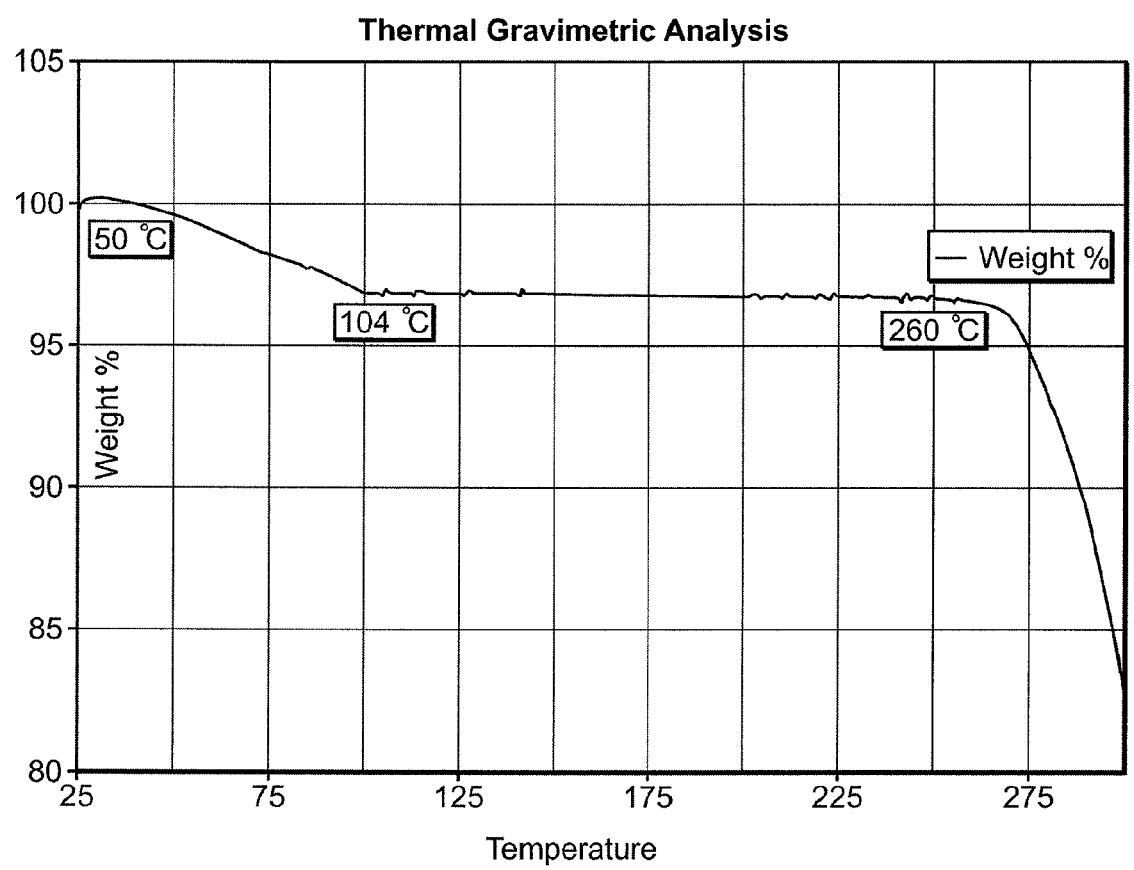
FIG. 2 illustrates analysis results for commercially available Reb D (hydrate) using Thermal Gravimetric Analysis (TGA).

In a complementary experiment, commercially available Reb D was examined by Thermal Gravimetric Analysis (TGA). TGA is a type of test that may be performed to determine changes in weight as a function of temperature. The method may be used to determine loss of water, or any other volatiles in a compound as it is heated. A derivative weight loss curve can be used to determine at what temperature weight loss is most apparent. A 2 mg sample was placed into a sample boat on a microgram balance (accurate to +/−1 μg) and heated while monitoring the mass. The temperature was increased at 10° C./min while continuing to monitor the mass and graphing the result as a percentage of the original mass. The results from this analysis are shown in FIG. 2 and indicate mass loss beginning at about 50° C. and continuing to about 104° C. and then remaining stable until reaching approximately 260° C., whereupon a large loss of mass was recorded, which corresponds to the decomposition temperature. These results are in agreement with those of the previously mentioned DSC analysis.

Figure 3:
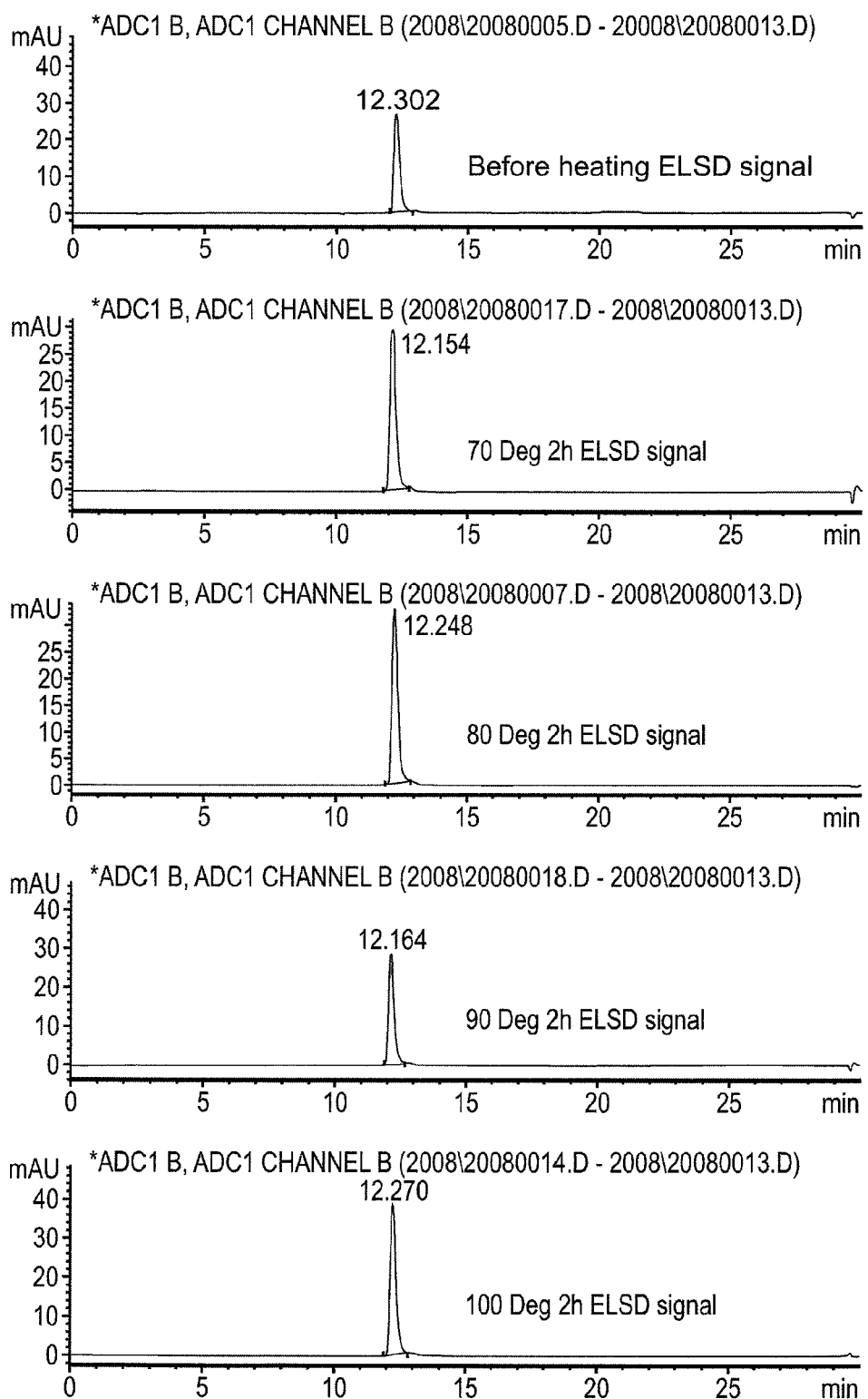
FIG. 3 illustrates HPLC chromatogram analysis results using ELSD detection of four samples of commercially available Reb D (hydrate) that underwent heating in an oven for two hours at a series of four temperatures: 70°, 80°, 90°, and 100° C.
Figure 4:
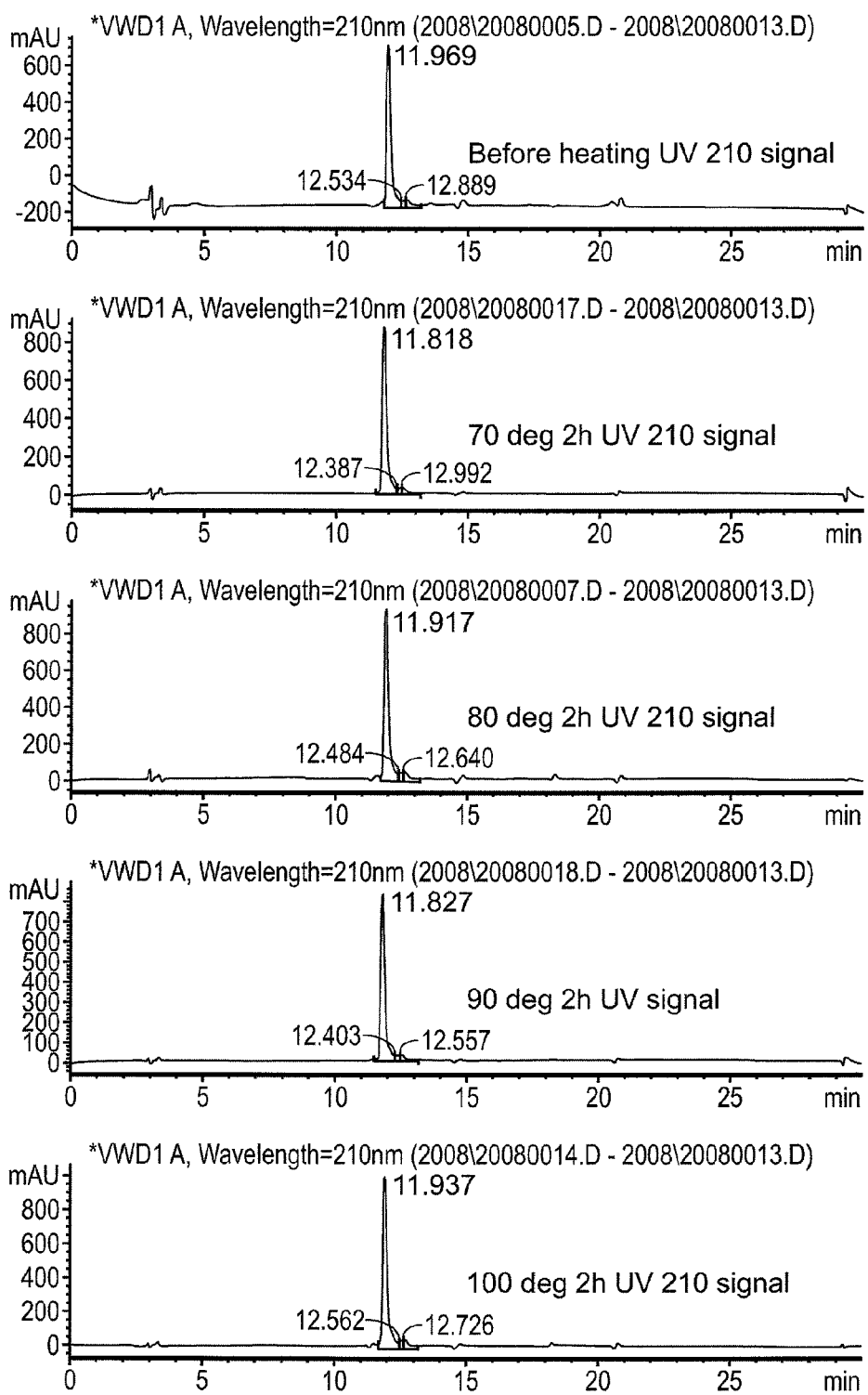
FIG. 4 illustrates HPLC chromatogram analysis results using UV detection for the four samples discussed in FIG. 3.

An experiment was performed on four samples (50 g each) of commercially available Reb D. The samples were each heated in an oven for two hours at one of four temperatures: 70°, 80°, 90° and 100° C. The samples were then immediately cooled and weighed to determine any loss in mass. Each sample, including the initial sample, was analyzed using gradient reversed-phase High Performance Liquid Chromatography (HPLC) with Evaporative Light Scattering Detection (ELSD) and Ultra-Violet (UV) detection methods to determine if any significant decomposition occurred. The results from this experiment are illustrated in Table 2 (see below) as well as in FIGS. 3 and 4.

TABLE 2

| Sample Temperature (° C.) | Sample Mass Initial (g) | Sample Mass End (g) | Net Loss (g) | Net Loss (weight %) |
|---|---|---|---|---|
| 70 | 50.08 | 49.89 | 0.19 | 0.38 |
| 80 | 50.05 | 49.82 | 0.24 | 0.48 |
| 90 | 50.11 | 49.73 | 0.38 | 0.76 |
| 100 | 50.01 | 49.33 | 0.68 | 1.36 |

The results indicate that in each of the four samples, a significant loss of mass occurred, but with little to no decomposition of the compound. Based on these series of experiments, the results indicate that water should be removed from the crystal structure of the compound at temperatures at least within the temperature range of 70°-105° C. without significant decomposition or change in the overall structure.

Figure 5:
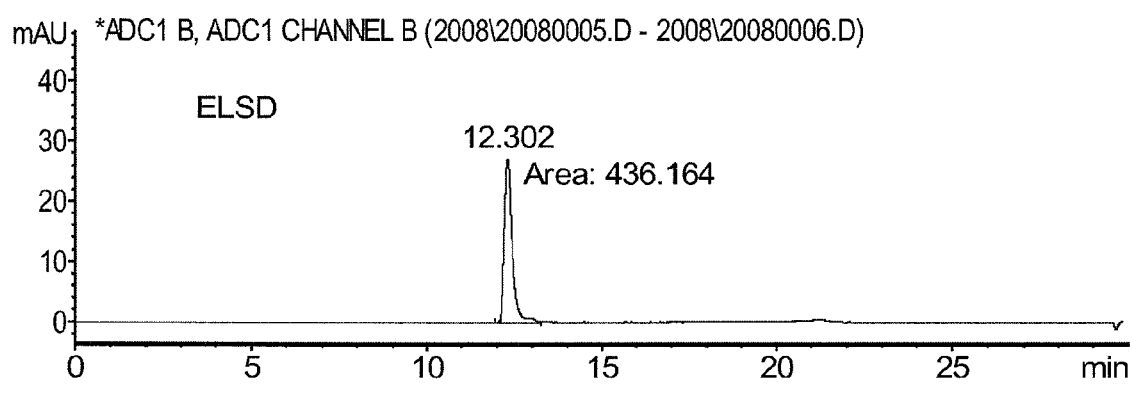
FIG. 5 illustrates HPLC chromatogram analysis results with both ELSD and UV detection methods for a sample of commercially available Reb D (hydrate) before undergoing the heating process.
Figure 5:
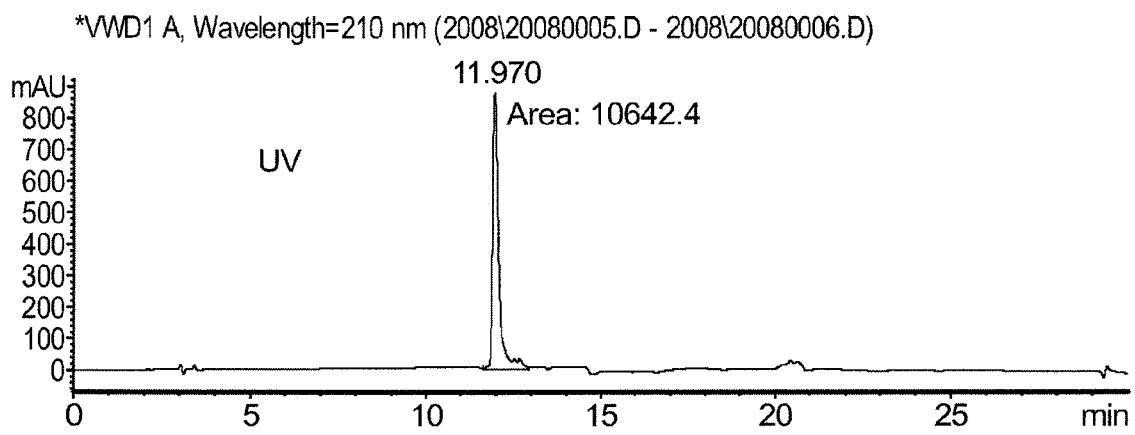
Figure 6:
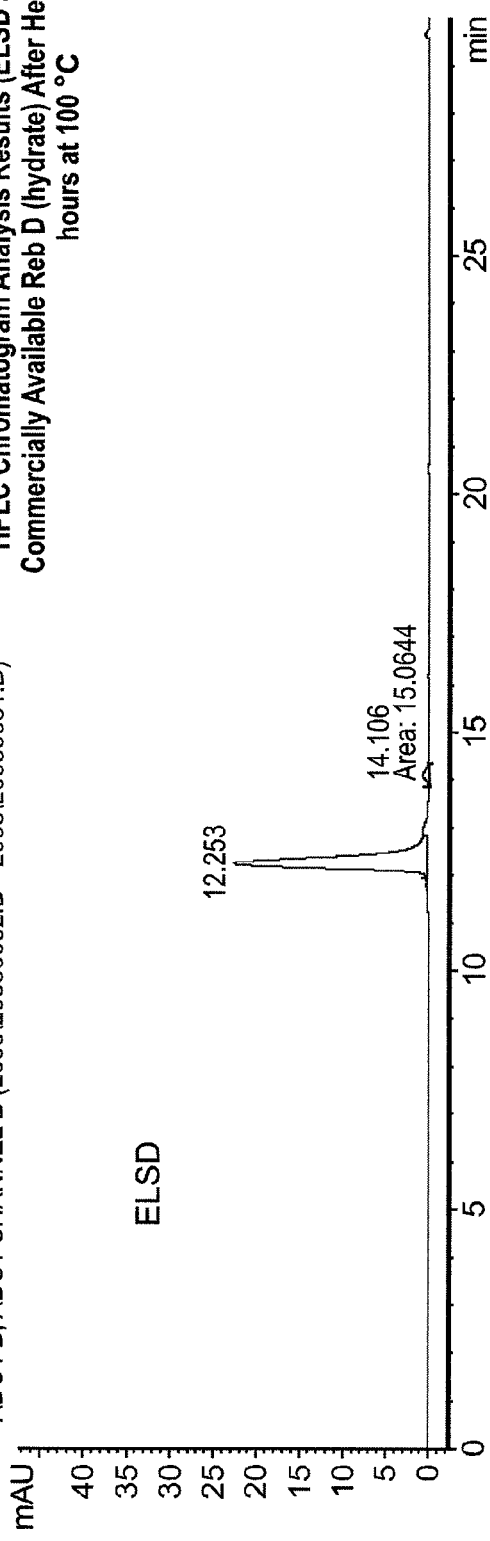
FIG. 6 illustrates HPLC chromatogram analysis results for both ELSD and UV detection methods on the Reb D sample discussed in FIG. 5 after it has undergone the process of heating for 120 hours at 100° C.
Figure 6:
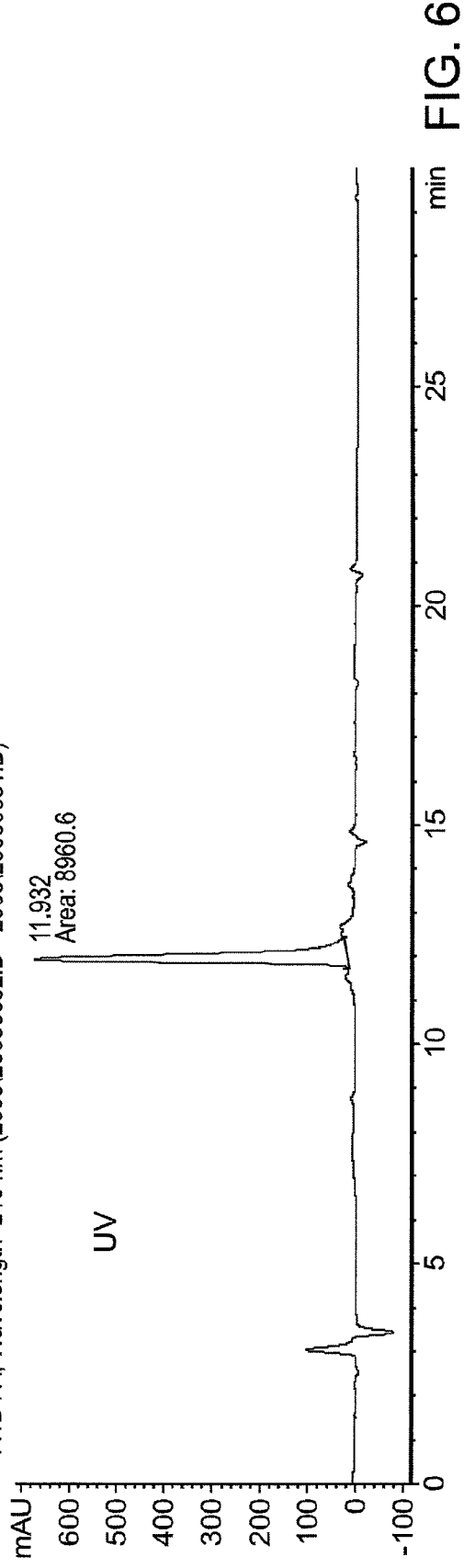

It was discovered that upon heating commercially available Reb D, believed to be a non-anhydrous form of Reb D (i.e., hydrate), compound in an oven to a temperature of 100° C. for 120 hours, a thermally stable anhydrous Reb D product was obtained. As illustrated in FIGS. 5 and 6, HPLC chromatogram analysis indicates that the thermally stable anhydrous form of Reb D has identical retention times to that of non-anhydrous Reb D. FIG. 5 shows the HPLC chromatogram analysis results with both ELSD and UV detection methods on Reb D before it undergoes the heating process. The top graph indicates ELSD detection, and the bottom graph indicates UV detection results taken at a wavelength of 210 nm. FIG. 6 shows the same analysis performed on an anhydrous sample of Reb D, i.e., after the sample has undergone the process of heating for 120 hours at 100° C. As indicated by the results in the figures, the two forms of Reb D have identical HPLC retention values, indicating that no significant level of decomposition of anhydrous Reb D has occurred. The HPLC chromatogram analysis in FIG. 6 reveals an impurity at the 14.1 minute elution mark that comprises about 5% of the total mass, but its structure has not been determined.

Figure 7:
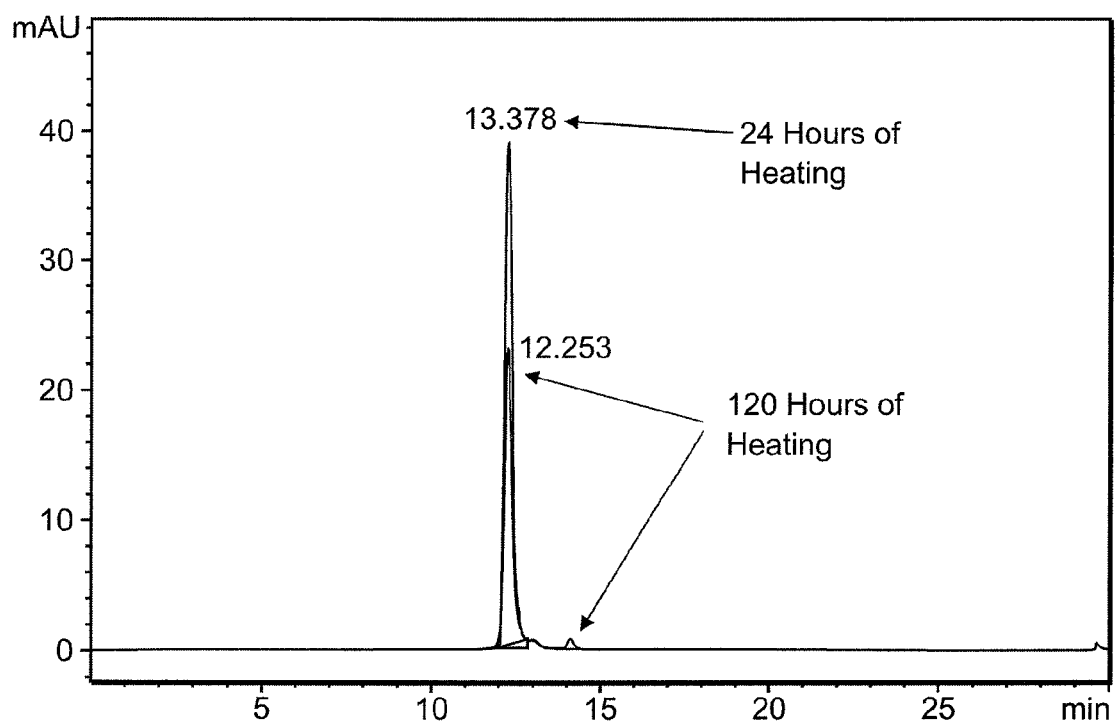
FIG. 7 illustrates an overlay of the HPLC chromatogram analysis results performed on samples of commercially available Reb D after having been heated for 24 hours and 120 hours at 100° C.

Additional HPLC chromatogram analysis was performed using both an anhydrous sample of Reb D (i.e., after the sample had undergone the process of heating for 120 hours at 100° C.) and a sample that had undergone heating for 24 hours. These results are illustrated in FIG. 7. FIG. 7 shows the overlay of the two results, with the lower peak corresponding to the results from the anhydrous Reb D sample (heated for 120 hours), and the taller peak corresponding to the results from the Reb D sample that had undergone heating for only 24 hours. A decomposition peak estimated to be in the range of 2% of the total mass was found in the analysis results from the anhydrous Reb D sample, but its structure was not determined. As indicated in FIG. 7, the two samples have identical HPLC retention values, indicating that no significant level of decomposition has occurred.

Figure 8:
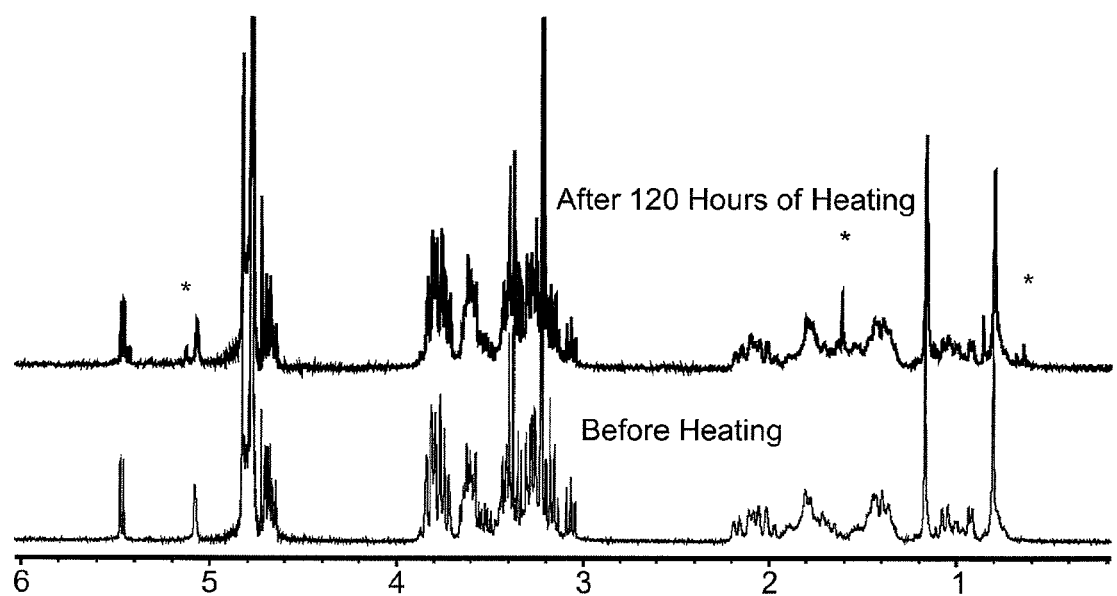
FIG. 8 illustrates an overlay of the proton NMR spectra analysis results for a sample of commercially available Reb D both before and after having been heated at 100° C. for 120 hours.

Furthermore, NMR analysis performed on Reb D samples both before and after the samples underwent heating indicate that the structure of the anhydrous form of Reb D is preserved. These results are illustrated in FIG. 8. which shows an overlay of the proton NMR spectrum analysis results for a Reb D sample both before it undergoes heating (bottom) and after it undergoes heating for 120 hours at 100° C. As clearly indicated in FIG. 8, the peaks are identical, indicating the preservation of the structural integrity of Reb D compound after undergoing the heating process.

Figure 9:
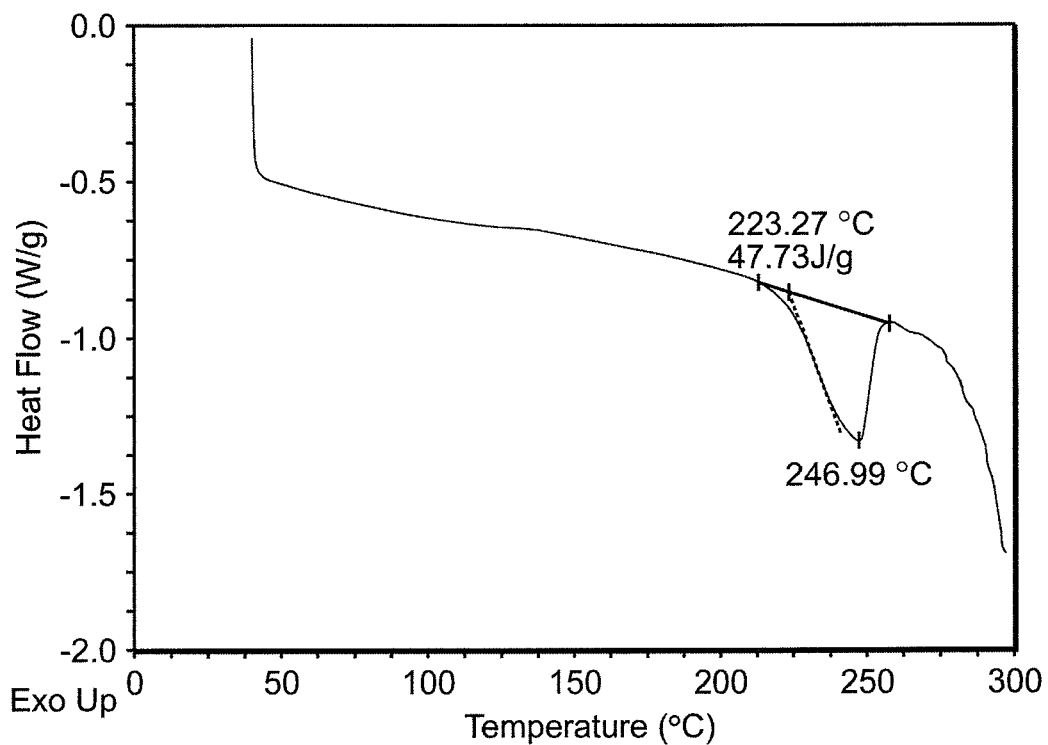
FIG. 9 illustrates a DSC thermal energy graph for anhydrous Reb D (i.e. commercially available Reb D after it has been heated for 120 hours at 100° C.).
Figure 10:
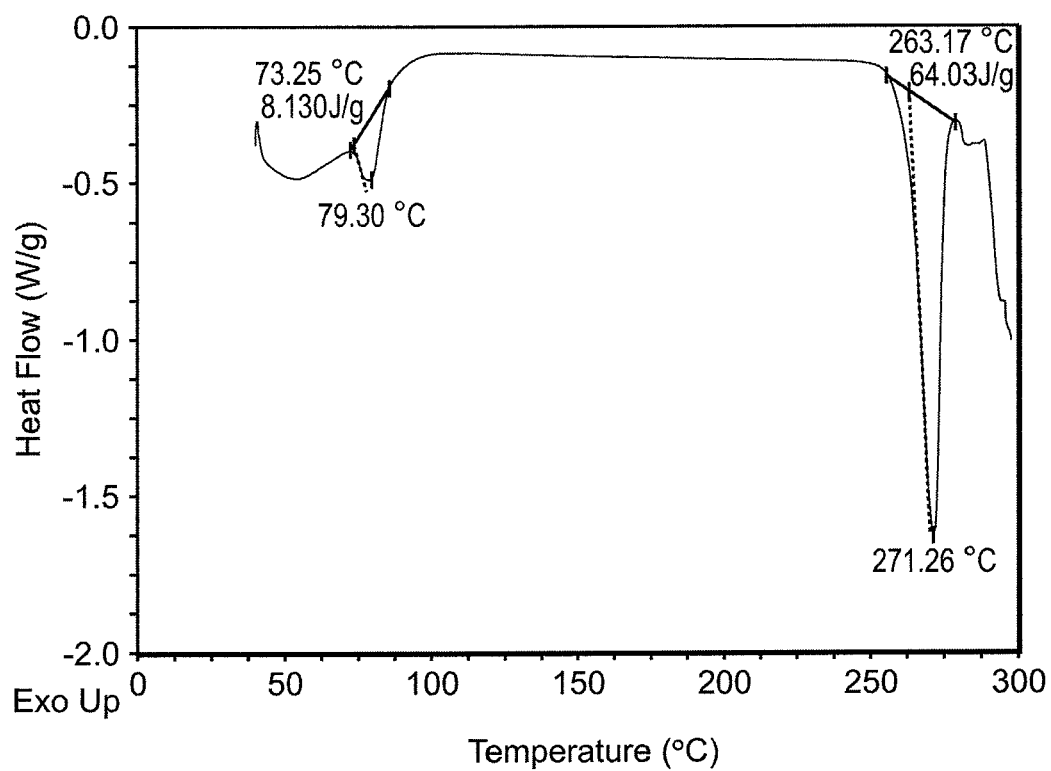
FIG. 10 illustrates a DSC thermal energy graph for commercially available Reb D after it has been heated for only 16 hours at 100° C.

DSC analysis for anhydrous Reb D (commercially available Reb D after undergoing heating for 120 hours at 100° C.) is illustrated in FIG. 9. In contrast to FIG. 1, anhydrous Reb D does not depict a thermal energy change between about 81°-104° C. This further supports the position that all of the water has been driven off, yielding a more soluble structure. Additional DSC analysis for a sample of Reb D that has undergone heating for 16 hours is shown in FIG. 10. Similar to the results shown in FIG. 1, a thermal energy change is shown to occur at temperatures ranging from about 73°-100° C. These results indicate that heating Reb D for 16 hours at 100° C. does not entirely eradicate the presence of the hydrate(s).

Figure 11:
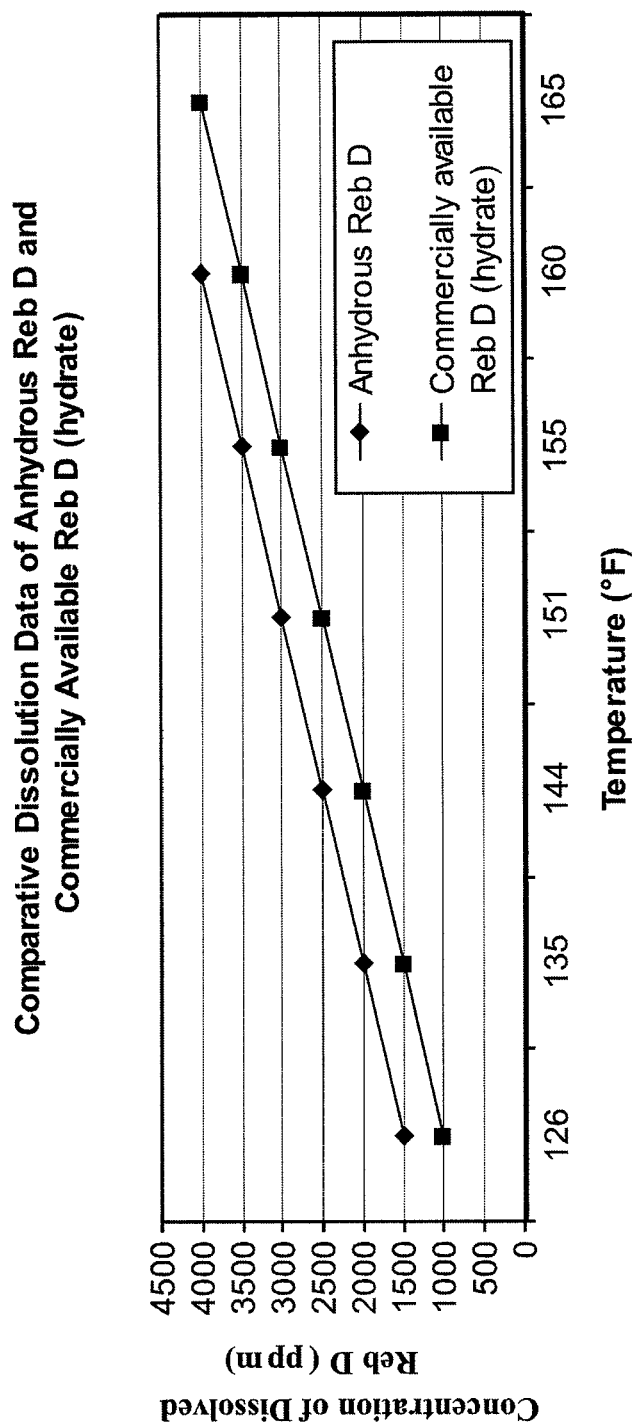
FIG. 11 summarizes the comparative dissolution data of both the anhydrous form of Reb D and the commercially available Reb D (hydrate).

A water solubility experiment was performed with both the anhydrous form of Reb D and the non-anhydrous form. Equal starting amounts of both substances were placed in equal volumes of water in side-by-side beakers equipped with overhead stirrers and hot plates. As the temperature of the water solution increased and the starting amounts were dissolved, incremental quantities of additional respective sweetener were added. FIG. 11 summarizes the solubility versus temperature relationship between the two forms of Reb D resulting from this experiment. The data in the graph clearly indicates that to achieve the same degree of solubility, anhydrous Reb D requires about 10°-15° C. less of heating. Also, after cooling to room temperature and sitting on a bench-top overnight, the water solution of Reb D hydrate was full of precipitate, whereas the water solution of anhydrous Reb D stayed as a clear solution.

Although one exemplary method to prepare anhydrous Reb D has been described above, it is to be understood that other methods and processing techniques for preparing anhydrous Reb D may also be utilized. Other methods of producing anhydrous Reb D are possible. Various factors, such as the quantity of the initial sample, may alter process conditions, e.g., the required length of time and/or the required temperature for heating. The subject matter defined in the appended claims is not necessarily limited to the specific features or acts described above. Rather, the specific features and methods described above are disclosed as example forms of implementing the claims. In addition, unless stated otherwise, all percentages recited in the description, disclosure and the appended claims are percent by weight of the fully formulated sweetener, syrup, component, food or beverage product, composition, solution and the like unless otherwise stated.

Certain aspects of this disclosure relate to "solubility," which is defined in a broad sense as the ability or tendency of one substance to dissolve into another. "The solubility" of a compound may also be expressed as the greatest amount of compound that will dissolve in a specified volume of solvent under particular conditions. The solubility of a compound may be total or fractional and varies depending on the physico-chemical characteristics of the solvent in which it is incorporated (e.g., temperature, pressure, pH, etc). Solvents suitable for use in certain exemplary embodiments disclosed here include, without limitation, water, alcohols (e.g., benzyl alcohol, methanol, ethanol, and isopropanol), citric acid, propylene glycol, glycerine, triacetin, limonene, suitable hydrocarbons, suitable substituted hydrocarbons, amines, aldehydes, esters, ketones, lactones, phenols, acids, nitrogen- and sulfur-containing compounds, and mixtures of any of them.

Certain aspects of this disclosure relate to the "concentration" of a solution, which is taken to mean the amount of solute in a given amount of solvent or solution. There are many ways to express concentration. For example, concentration may be defined in units of mass per unit volume (e.g., mg/mL, mg/cm3 and the like), percent by mass (which is simply the mass of the solute divided by the total mass of the solution multiplied by 100% (e.g., weight percent, percent by weight, wt %, w/w, and the like)), percent by volume (which is simply the volume of the solute divided by the sum of the volumes of the other components multiplied by 100% (e.g., volume percent, percent by volume, v/v, and the like)), molarity (which is the number of moles of solute dissolved in one liter of solution), molality (which is the number of moles of solute dissolved in one kilogram of solvent), and parts per million (which is defined as the mass of the component in solution divided by the total mass of the solution multiplied by $10^6$ (e.g., ppm)). A "saturated" solution is a solution in which the concentration of dissolved solute is equal to that which would be in equilibrium with un-dissolved solute under the given conditions, e.g., temperature and pressure.

The compound suitable for use in at least certain exemplary embodiments of the sweeteners, solutions, components, products, compositions and methods disclosed here is understood to represent the formula:

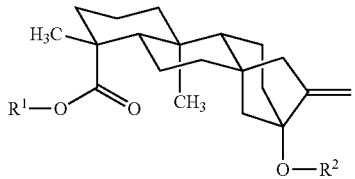

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl. The compound with this formula may also be referred to here and in the appended claims as Reb D.

As used with reference to forms of Rebaudioside D disclosed here, the term "anhydrous" means substantially anhydrous and, more specifically, either no or a reduced amount of hydrates associated with the Rebaudioside D such that it has the property or characteristic of forming, with heating, a stable aqueous solution of greater than 500 ppm. Certain exemplary embodiments of the anhydrous Rebaudioside D disclosed here have the property or characteristic of forming, with heating, a stable aqueous solution of greater than 1,000 ppm. Certain exemplary embodiments of the anhydrous Rebaudioside D disclosed here have the property or characteristic of forming, with heating, a stable aqueous solution of greater than 1500 ppm. Certain exemplary embodiments of the anhydrous Rebaudioside D disclosed here have the property or characteristic of forming, with heating, a stable aqueous solution of greater than 2,000 ppm. Certain exemplary embodiments of the anhydrous Rebaudioside D disclosed here have the property or characteristic of forming, with heating, a stable aqueous solution of greater than 2500 ppm. Certain exemplary embodiments of the anhydrous Rebaudioside D disclosed here have the property or characteristic of forming, with heating, a stable aqueous solution of greater than 3,000 ppm. Hygroscopic activity may cause water to be absorbed into a quantity of anhydrous Rebaudioside D upon exposure to moisture, including, e.g., exposure over time to water vapor in the ambient atmosphere. An elemental analysis of anhydrous Rebaudioside D may show water for that reason. Rebaudioside D which has absorbed water due to hygroscopic activity is nevertheless anhydrous as that term is used here, if it has either no or a reduced amount of hydrates such as to have the property or characteristic of forming, with heating, a stable aqueous solution, as set forth above. The anhydrous compound suitable for use in at least certain exemplary embodiments of the sweeteners, solutions, components, products, compositions and methods disclosed here is understood to represent the formula:

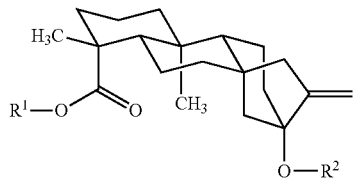

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl. The compound with this formula may also be referred to here and in the appended claims as anhydrous Reb D.

As used here and in the appended claims, the term "non-anhydrous form of the compound" or "non-anhydrous compound" includes any or all forms of the compound wherein water is attached, e.g., hydrates, monohydrates, dihydrates and trihydrates, or mixtures of any of these, as well as any other forms of the compound that may form in between the water-free and the fully hydrated form (i.e., the form which cannot bind additional water) of the compound. The non-anhydrous compound suitable for use in at least certain exemplary embodiments of the sweeteners, solutions, components, products, compositions and methods disclosed here is understood to represent the formula:

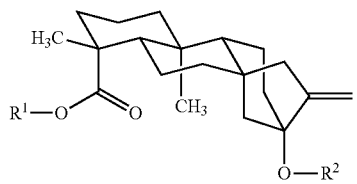

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl. The compound with this formula may also be referred to here and in the appended claims as non-anhydrous Reb D.

Testing of the anhydrous Reb D compound disclosed here has indicated that it is more soluble than some or all of the non-anhydrous forms of the compound. For example: a test of commercially available Reb D compound (believed to be a non-anhydrous form of Reb D) wherein the non-anhydrous form was dissolved in water with heating and allowed to cool resulted in Reb D precipitating out of solution within a number of hours, leaving the solution concentration at a level less than 500 ppm (e.g., 450 ppm). In contrast, testing of anhydrous Reb D, wherein the Reb D is dissolved in water with heating, has found that a solution concentration of 3000 ppm can be achieved with no Reb D precipitating out of solution after the solution has cooled and remained at room temperatures for a time period of at least 24 hours.

In certain exemplary embodiments, the solubility of anhydrous compound in water is at least 500 ppm and up to about 3000 ppm or more while maintaining the water at room temperatures. Once dissolved, the compound remains in solution for a period of time of at least 24 hours at room temperature without forming a precipitate.

As used here and in the appended claims, "room temperature" is defined as temperatures at least within the temperature range of 68° F.-77° F. (20° C.-25° C.), e.g., 68° F., unless otherwise stated.

It should be understood that as used here and in the appended claims, the phrase "the anhydrous compound is more soluble in water at temperatures at least within the temperature range of 135°-150° F. than a non-anhydrous form of the compound" is taken to mean that at least a portion of the anhydrous compound has a better ability to dissolve or be solubilized by water than a non-anhydrous form of the compound at all temperatures within the cited range.

As used here and in the appended claims, the terms "sweetener" or "sweetener component" are edible compositions suitable for consumption in solutions, components, food or beverage products, and compositions included in the disclosure and which are capable of providing sweetness. The sweetener or sweetener component may include, but is not limited to, nutritive, non-nutritive, natural, artificial, synthetic, potent, and any combination thereof. As used herein, a "non-nutritive sweetener" is one which does not provide significant caloric content in typical usage amounts, e.g., one which imparts less than 5 calories per 8 oz. serving of beverage product to achieve the sweetness equivalent of 10 Brix of sugar. As used herein, a "potent sweetener" means a sweetener which is at least twice as sweet as sugar (sucrose), that is, a sweetener which on a weight basis requires no more than half the weight of sugar to achieve an equivalent sweetness. For example, a potent sweetener may require less than one-half the weight of sugar to achieve an equivalent sweetness in a beverage product sweetened to a level of 10 degrees Brix with sugar.

In certain exemplary embodiments of the sweetener disclosed here, the sweetener or sweetener component comprises anhydrous Reb D at concentrations of at least 50%, at least 75% by weight, or at least 90% by weight of the sweetener or sweetener composition.

Certain exemplary embodiments of the methods disclosed here comprise forming beverage products with sweetener at concentrations of at least 500 ppm, at least 1000 ppm, at least 1500 ppm, at least 2000 ppm, at least 2500 ppm, or at least 3000 ppm at room temperature (68°-77° F.).

In certain exemplary embodiments of the solutions, food or beverage products, and compositions disclosed here, the sweetener or sweetener composition may comprise at least Reb D, and optionally filler, bulking agents (e.g., dextrose, maltodextrin, erythritol, tagatose, polydextrose, and the like), anti-caking agent, and any combination thereof.

In certain exemplary embodiments of the solutions, components, food or beverage products, and compositions disclosed here, Reb D is used as a sweetener, either alone or in conjunction with other sweeteners. Other sweeteners or combinations of sweeteners suitable for use in combination with Reb D may be selected for the desired nutritional characteristics, taste profile, mouthfeel and/or other organoleptic factors. Non-nutritive sweeteners suitable for use in at least certain embodiments include, but are not limited to, peptide based sweeteners, e.g., aspartame, neotame, and alitame, and non-peptide based sweeteners, for example, sodium saccharin, calcium saccharin, acesulfame (including, but not limited to acesulfame potassium), cyclamate (including, but not limited to sodium cyclamate and/or calcium cyclamate), neohesperidin dihydrochalcone, and sucralose, sorbitol, mannitol, xylitol, glycyrrhizin, neohesperidin dihydrochalcone, D-tagatose, erythritol, meso-erythritol, malitol, maltose, lactose, fructo-oligosaccharides, Lo Han Guo ("LHG"), steviol glycosides, e.g., steviosides and Rebaudiosides other than Reb D (including, but not limited to e.g., Reb A, Reb B, Reb C, and Reb E), and other dipeptides (e.g. neotame), saccharin, xylose, arabinose, isomalt, lactitol, maltitol, trehalose, and ribose, and protein sweeteners such as thaumatin, monellin, monatin, brazzein, L-alanine and glycine, related compounds and mixtures of any of them. It will be within the ability of those skilled in the art, given the benefit of this disclosure, to select suitable additional or alternative sweeteners for use in various embodiments of the beverage products disclosed here.

As mentioned above, at least certain exemplary embodiments of the sweeteners, solutions, components, food or beverage products and compositions disclosed here employ Reb D, and can include stevioside, other steviol glycosides in addition to Reb D, or related compounds or mixtures of any of them for sweetening. These compounds, including Reb D, can be obtained by extraction or the like from the stevia plant. Stevia (e.g., Stevia rebaudiana Bertoni) is a sweet-tasting plant. The leaves contain a complex mixture of natural sweet diterpene glycosides. The following nonsweet constituents also have been identified in the leaves of stevia plants: labdane, diterpene, triterpenes, sterols, flavonoids, volatile oil constituents, pigments, gums and inorganic matter.

As used here and in the appended claims, the term "edible composition" means a food or beverage product or an ingredient of a food or beverage product suitable for human or animal consumption. Exemplary beverage products include, but are not limited to, any ingredient or any combination of ingredients, or any substance or any combinations of substances, that can be used or prepared for use as a beverage for a mammal and includes, but is not limited to, ready to drink liquid formulations, beverage concentrates, syrups, powders and the like. Exemplary beverage products include, but are not limited to, carbonated and non-carbonated beverages, fountain beverages, frozen ready-to-drink beverages, frozen carbonated beverages, beverage concentrates, powdered concentrates, coffee beverages, tea beverages, dairy beverages, flavored waters, enhanced waters, fruit juices, fruit juice-flavored drinks, fruit-flavored drinks, sports drinks, soy drinks, hydration drinks, energy drinks, fortified/enhanced water drinks, vegetable drinks, grain-based drinks, malt beverages, fermented drinks, yogurt drinks, kefir, alcoholic beverages, and mixtures of any of them. Exemplary fruit juice sources include citrus fruit, e.g. orange, grapefruit, lemon and lime, berry, e.g. cranberry, raspberry, blueberry and strawberry, apple, grape, pineapple, prune, pear, peach, cherry, mango, and pomegranate. Beverage products further include, e.g., full calorie drinks/beverages and reduced-calorie (e.g., light, diet, zero calorie) drinks/beverages. Beverage products include bottle, can, and carton products and fountain syrup applications.

In certain exemplary embodiments, additional ingredients may be added to the sweeteners, solutions, components, food or beverage products, and compositions disclosed here. These additional ingredients may also be referred to as food or beverage ingredients and include, but are not limited to acidulants, colorants, flavorants, minerals, vitamins, fruit juices, fruit flavors, or other fruit products, other taste modifiers, e.g., tastents, masking agents and the like, flavor enhancers, and/or carbonation, any of which typically can be added to various sweeteners, solutions, components, or food or beverage products to vary the taste, mouthfeel, nutritional characteristics, etc. Exemplary flavorants which may be suitable as beverage ingredients for at least certain beverage products in accordance with this disclosure include cola flavor, tea flavor, citrus flavor, berry flavor, spice flavor and others. Carbonation in the form of carbon dioxide may be added for effervescence. Preservatives can be added if desired, depending upon the other ingredients, production technique, desired shelf life, etc. Optionally, caffeine can be added. The beverage products of the present invention may also contain other ingredients including, without limitation, vitamins, natural buffering agents, e.g., the sodium and potassium salts of citric, tartaric, and lactic acids, natural preservatives, e.g., nisin, cinnamic acid, etc., natural salts, thickeners, and natural anti-foaming agents. Additional and alternative suitable ingredients will be recognized by those skilled in the art given the benefit of this disclosure.

The terms "beverage concentrate," and "syrup" are used interchangeably throughout this disclosure. At least certain exemplary embodiments of the beverage products contemplated are prepared with an initial volume of water to which additional beverage ingredients are added. Full strength beverage products can be formed from the beverage concentrate by adding further volumes of water to the concentrate (also known as diluting). Typically, for example, full strength beverage products can be prepared from the concentrates by combining approximately 1 part concentrate with between approximately 3 to approximately 7 parts water. In certain exemplary embodiments the full strength beverage product is prepared by combining 1 part concentrate with 5 parts water. In certain exemplary embodiments the additional water used to form the full strength beverages is carbonated water. In certain other embodiments, a full strength beverage is directly prepared without the formation of a concentrate and subsequent dilution.

As used here and in the appended claims, "sweetened syrup" is defined as syrup that possesses sweetness, and comprises at least one or more sweeteners. In certain exemplary embodiments of the sweetened syrups disclosed here, the sweetener comprises at least Reb D.

It should be understood that exemplary embodiments of the sweeteners, solutions, components, products, compositions and methods in accordance with this disclosure may have any of numerous specific formulations or constitutions. For example, the method for forming syrup may vary to a certain extent, depending upon such factors as the end product's intended market segment, its desired nutritional characteristics, flavor profile and the like. For example, it will be an option to add further ingredients to the formulation of a particular solution or beverage product comprising at least some amount of the syrup. Additional (i.e., more and/or other) sweeteners may be added, flavorings, electrolytes, vitamins, fruit juices or other fruit products, tastents, masking agents and the like, flavor enhancers, and/or carbonation typically can be added to any such solutions or products to vary the taste, mouthfeel, nutritional characteristics, etc. Exemplary flavorings which may be suitable for at least certain solutions and products in accordance with this disclosure include cola flavoring, citrus flavoring, spice flavorings and others. Additional and alternative suitable ingredients will be recognized by those skilled in the art given the benefit of this disclosure.

As used here and in the appended claims "aqueous solution" is defined as any solution in which water is all or some of the dissolving medium or solvent. The solution may optionally, in addition to water, comprise other liquids in varying amounts. In exemplary embodiments of the methods disclosed here, the aqueous solution comprises at least 50% by weight water, at least 75% by weight water, at least 90% by weight, or at least 95% by weight.

In at least certain exemplary embodiments of the invention, a "supersaturated aqueous solution" disclosed here and in the appended claims may include anhydrous Reb D. A "supersaturated aqueous solution" refers to a solution that contains more of the dissolved compound than could be dissolved by the water under normal circumstances. In other words, the solution contains an amount of a compound greater than that required for saturation as a result of having been cooled from a higher temperature to a temperature below that at which saturation occurs. Certain exemplary embodiments of the methods disclosed here comprise forming at room temperature (68°-77° F.) supersaturated solutions of Reb D at concentrations of at least 500 ppm, at least 1000 ppm, at least 1500 ppm, at least 2000 ppm, at least 2500 ppm, or at least 3000 ppm. Solutions referenced to as supersaturated both here and in the appended claims are such that the concentration of Reb D is higher than that achieved with heating and higher than that can be dissolved without heating.

Water is a basic food and beverage ingredient used in the sweeteners, syrups, solutions, beverages, components, products, compositions and methods disclosed here. Water may comprise a certain concentration of dissolved compound, and typically acts as the vehicle or liquid portion in which the remaining ingredients are dissolved, emulsified, suspended or dispersed. Purified water can be used in the manufacture of certain embodiments of the beverage product, and water of a standard beverage quality can be employed in order not to adversely affect beverage product taste, odor, or appearance. The water typically will be clear, colorless, and free from objectionable minerals, tastes and odors, free from organic matter, low in alkalinity and of acceptable microbiological quality based on industry and government standards applicable at the time of producing the beverage. Water suitable for certain exemplary embodiments included in this disclosure may also be carbonated.

Certain embodiments of the sweeteners, syrups, solutions, food or beverage products, components, and compositions disclosed here comprising Reb D may also include one or more acids. An acidulant can serve any of one or more functions, including, for example, lending tartness to the taste of the beverage product, enhancing palatability, increasing thirst quenching effect, modifying sweetness and acting as a mild preservative. Suitable acids are known and will be apparent to those skilled in the art given the benefit of this disclosure. Exemplary acids suitable for use in certain embodiments of the beverage products disclosed here include, but are not limited to, phosphoric acid, citric acid, malic acid, tartaric acid, lactic acid, ascorbic acid, fumaric acid, gluconic acid, succinic acid, maleic acid and adipic acid and mixtures of any of them. The acid can be used in solution form, for example, and in an amount sufficient to provide the desired pH of the beverage product. Typically, for example, the one or more acids of the acidulant are used in amount, collectively, of from about 0.01% to about 0.5% by weight of the beverage, e.g., from about 0.05% to about 0.25% by weight of the beverage, depending upon the acidulant used, desired pH, other ingredients used, etc. The pH of at least certain exemplary embodiments of the beverage products disclosed here can be a value within the range of from at least 2.0 to about 5.0. The acid in certain exemplary embodiments enhances beverage product flavor. Too much acid can impair the beverage product flavor and result in sourness or other off-taste, while too little acid can make the beverage product taste flat. The particular acid or acids chosen and the amount used will depend, in part, on the other ingredients, the desired shelf life of the beverage product, as well as effects on the beverage product pH, titratable acidity, and taste. It will be within the ability of those skilled in the art, given the benefit of this disclosure, to select a suitable acid or combination of acids and the amounts of such acids for the acidulant component of any particular embodiment of the beverage products disclosed here.

Certain exemplary embodiments of the sweeteners, syrups, solutions, food or beverage products, components and compositions disclosed here may also contain small amounts of buffering agents to adjust pH. Such agents include, but are not limited to, e.g., the sodium and potassium salts of citric, tartaric, and lactic acids. The amount included will depend on the type of buffering agents and on the degree to which the pH is to be adjusted.

The sweeteners, syrups, solutions, food or beverage products, components, and compositions disclosed here may optionally contain one or more additional flavor compositions, for example, natural and synthetic fruit flavors, botanical flavors, other flavors, and mixtures thereof. As used here, the term "fruit flavor" refers generally to those flavors derived from the edible reproductive part of a seed plant. Included are both those wherein a sweet pulp is associated with the seed, e.g., banana, tomato, cranberry and the like, and those having a small, fleshy berry. Also included within the term "fruit flavor" are synthetically prepared flavors made to simulate fruit flavors derived from natural sources. Examples of suitable fruit sources include whole fruits or portions thereof, fruit juice, fruit juice concentrates, fruit purees and blends thereof, dried fruit powders, dried fruit juice powders, freeze dried fruit juices, powders and purees and the like.

Exemplary fruit flavors include the citrus flavors, e.g., orange, mandarin orange, tangerine, tangelo, pomelo, lemon, lime and grapefruit, and such flavors as apple, grape, cherry, and pineapple flavors and the like, and any combination thereof. In certain exemplary embodiments the solutions, food or beverage products, and compositions disclosed here comprise a fruit flavor component, e.g., juice concentrate or juice. As used here, the term "botanical flavor" refers to flavors derived from parts of a plant other than the fruit. As such, botanical flavors can include those flavors derived from essential oils and extracts of nuts, bark, roots and leaves. Also included within the term "botanical flavor" are synthetically prepared flavors made to simulate botanical flavors derived from natural sources. Examples of such botanical flavors include cola flavors, tea flavors, coffee, cocoa, hazelnut, almond, other nut flavors, and mixtures thereof. The flavor component can further comprise a blend of the above-mentioned flavors. In certain exemplary embodiments of the solutions, food or beverage products, and compositions described here, a cola flavor component and/or a tea flavor component is used. The particular amount of the flavor component useful for imparting flavor characteristics to the solution, food or beverages product, or composition will depend upon the flavor(s) selected, the flavor impression desired, and the form of the flavor component. Those skilled in the art, given the benefit of this disclosure, will be readily able to determine the amount of any particular flavor component(s) used to achieve the desired flavor impression.

Other flavorings suitable for use in at least certain exemplary embodiments of the sweeteners, syrups, solutions, food or beverage products, components, and compositions disclosed here include, e.g., spice flavorings, such as cassia, clove, cinnamon, pepper, ginger, vanilla spice flavorings, cardamom, coriander, root beer, sassafras, ginseng, and others. Numerous additional and alternative flavorings suitable for use in at least certain exemplary embodiments will be apparent to those skilled in the art given the benefit of this disclosure. Flavorings can be many forms, including, but not limited to an extract, oleoresin, juice concentrate, bottler's base, or other forms known in the art.

The one or more flavorings can be used in the form of an emulsion. A flavoring emulsion can be prepared by mixing some or all of the flavorings together, optionally together with food or beverage ingredients, and an emulsifying agent. The emulsifying agent may be added with or after the flavorings mixed together. In certain exemplary embodiments the emulsifying agent is water-soluble. Exemplary suitable emulsifying agents include, but are not limited to gum acacia, modified starch, carboxymethylcellulose, gum tragacanth, gum ghatti and other suitable gums. Additional suitable emulsifying agents will be apparent to those skilled in the art, given the benefit of this disclosure.

Weighting agents, which can also act as clouding agents, are typically used to keep emulsion droplets dispersed in a beverage product. Examples of such weighting agents include, but are not limited to brominated vegetable oils, rosin esters and, in particular, ester gums. Any weighting agent that is commercially available can be used in beverages products disclosed here. Besides weighting agents, emulsifiers and emulsion stabilizers can be used to stabilize the flavor emulsion droplets. Examples of such emulsifiers and emulsion stabilizers include, but are not limited to gums, pectins, cellulose, polysorbates, sorbitan esters and propylene glycol alginates.

Carbon dioxide is used to provide effervescence to certain exemplary embodiments of the sweeteners, syrups, solutions, food or beverage products, components, and compositions disclosed here. Any of the techniques and carbonating equipment known in the art for carbonating food or beverage products can be employed. Carbon dioxide can enhance the food or beverage product taste and appearance and can aid in safeguarding the beverage product purity by inhibiting and destroying objectionable bacteria. In certain embodiments, for example, the beverage product has a $CO_2$ level up to about 7.0 volumes carbon dioxide. Typical embodiments may have, for example, from about 0.5 to 5.0 volumes of carbon dioxide. As used here and in the appended claims, one volume of carbon dioxide is defined as the amount of carbon dioxide absorbed by any given quantity of water at 60° F. (16° C.) temperature and atmospheric pressure. A volume of gas occupies the same space as does the water by which it is absorbed. The carbon dioxide content can be selected by those skilled in the art based on the desired level of effervescence and the impact of the carbon dioxide on the taste or mouthfeel of the beverage product and the carbonation may be natural or synthetic.

Optionally, caffeine may be added to various embodiments of the sweeteners, syrups, solutions, food or beverage products, components, and compositions disclosed here. The amount of caffeine added is determined by the desired solution, food or beverage product, or composition properties, as well as any applicable regulatory provisions of the country where the solution, food or beverage product, or composition is to be marketed, etc. The caffeine must be of purity acceptable for use in foods and beverage products. The caffeine can be natural (e.g., from kola, cocoa nuts, coffee and/or tea) or synthetic in origin. The amount of caffeine can be from about 0.002% to about 0.05% by weight of the single strength beverage. In certain embodiments, the amount of caffeine is from about 0.005% to about 0.02%. In certain exemplary embodiments caffeine is included at a level of 0.02% or less by weight of the beverage product. For beverage concentrates or syrups, the caffeine level can be from about 0.006% to about 0.15%. Caffeine levels can be higher, for example, if flavored coffees which have not been decaffeinated are used since these materials contain caffeine naturally.

Examples of nutritional supplement ingredients suitable for the sweeteners, syrups, solutions, food or beverage products, components, and compositions disclosed here are known to those of ordinary skill in the art and include, without limitation, vitamins, minerals, herbs or botanicals, amino acids, or essential fatty acids or enzymes, proteases, tissues, organs, glands or portions thereof. Vitamins include, but are not limited to, vitamin A, vitamin D, vitamin E (tocopherol), vitamin C (ascorbic acid), vitamin $B_1$ (thiamine), vitamin $B_2$ (riboflavin), vitamin $B_3$ (niacin), vitamin $B_5$ (pantothenic acid), vitamin $B_6$ (pyridoxine), vitamin $B_7$ (biotin), vitamin $B_9$ (folic acid), vitamin $B_{12}$ (cyanocobalamin), vitamin K (naphthoquinone), vitamin D ($D_1$ (molecular compound of ergocalciferol with lumisterol, 1:1); $D_2$ (ergocalciferol or calciferol); $D_3$ (cholecalciferol); $D_4$ (dihydrotachysterol); $D_5$ (sitocalciferol)), and combinations thereof. Supplements are typically present in amounts generally accepted under good manufacturing practices and are typically present in amounts between about 1% to about 100% RDV, where such RDV are established. In certain embodiments, the nutritional supplement ingredient(s) may be present in an amount of from about 5% to about 20% RDV, where established.

Certain exemplary sweeteners, syrups, solutions, food or beverage products, components, and compositions disclosed here can optionally further include one or more colorants. As used herein, the "colorant" is intended to mean any compound that imparts color, which includes, but is not limited to natural pigments, synthetic pigment, color additives and mixtures thereof. Natural and artificial colors may be used. One or more FD&C dyes (e.g., yellow #5, blue #2, red #40) and/or FD&C lakes can be used to color solutions, food or beverage products, or compositions disclosed here. Exemplary lake dyes which may be used include, but are limited to, the FDA-approved Lake, such as Lake red #40, yellow #6, blue #1, and the like. Additionally, a mixture of FD&C dyes or a FD&C lake dye in combination with other conventional food and food colorants may be used. Examples of other coloring agents, include, but are not limited to natural agents, fruit and vegetable juices and/or powders, caramel color, riboflavin, carotenoids (for example, beta-carotene), tumeric, and lycopenes. The exact amount of coloring agent used will vary, depending on the agents used and the intensity desired in the finished product. Generally, if utilized, the coloring agent should be present at a level of from about 0.0001% to about 0.5%, from about 0.001% to about 0.1%, or from about 0.004% to about 0.1%, by weight or volume of the composition.

Preservatives may be used in at least certain embodiments of the sweeteners, syrups, solutions, food or beverage products, components, and compositions disclosed here. Solutions with a pH below 4 and especially those below 3 typically are "microstable," i.e., they resist growth of microorganisms, and so are suitable for longer term storage prior to consumption without the need for further preservatives. However, an additional preservative system can be used if desired. If a preservative system is used, it can be added to the solution, food or beverage product, or composition at any suitable time during production, e.g., in some cases prior to the addition of the sweetener. As used here, the terms "preservation system" or "preservatives" include all suitable preservatives approved for use in food and beverage products, including, without limitation, such known chemical preservatives as benzoates, e.g., sodium, calcium, and potassium benzoate, sorbates, e.g., sodium, calcium, and potassium sorbate, citrates, e.g., sodium citrate and potassium citrate, polyphosphates, e.g., sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and any combination thereof.

Preservatives can be used in amounts not exceeding mandated maximum levels under applicable laws and regulations. The level of preservative used typically is adjusted according to the planned final product pH, as well as an evaluation of the microbiological spoilage potential of the particular solution, food or beverage product, or composition formulation. In certain exemplary embodiments of the beverage product disclose here, the maximum level employed typically is about 0.05% by weight of the beverage product. It will be within the ability of those skilled in the art, given the benefit of this disclosure, to select a suitable preservative or combination of preservatives for solutions, food or beverage products, and compositions according to this disclosure.

Other methods of solution, food or beverage product, and composition preservation suitable for at least certain exemplary embodiments disclosed here include, e.g., heat treatment or thermal processing steps, such as hot filling and tunnel pasteurization. Such steps can be used to reduce yeast, mold and microbial growth in the beverage products. For example, U.S. Pat. No. 4,830,862 to Braun et al. discloses the use of pasteurization in the production of fruit juice beverages as well as the use of suitable preservatives in carbonated beverages. U.S. Pat. No. 4,925,686 to Kastin discloses a heat-pasteurized freezable fruit juice composition which contains sodium benzoate and potassium sorbate.

In certain exemplary embodiments, the sweeteners, syrups, solutions, food or beverage products, components, or compositions disclosed here may be provided in the form of juice. Juices can be employed in the form of a concentrate, puree, single-strength juice, or other suitable forms. The term "juice" as used here includes single-strength fruit and/or or vegetable juice, as well as concentrates, purees, milks, and other forms. Multiple different fruit and/or vegetable juices can be combined, optionally along with other flavorings, to generate a beverage product having the desired flavor. Examples of suitable juice sources include, but are not limited to, plum, prune, fig, pineapple, peach, banana, apple, pear, guava, apricot, coconut, olive, kiwi, quince, buckthorn, passion fruit, rowan, pomegranate, persimmon, mango, rhubarb, papaya, litchi, lemon, orange, lime, tangerine, mandarin orange, tangelo, pomelo, grapefruit, Barbados cherry (acerola cherry), bearberry, blackberry, blueberry, boysenberry, cherry, choke cherry, cloudberry, cranberry, current, date, dewberry, elderberry, grape, gooseberry, huckleberry, loganberry, olallieberry, mulberry, raisin, plains berry, prairie berry, raspberry, Saskatoon berry, salmonberry, Seabuckthorn berry, sloe berry, strawberry, thimbleberry, Thornberry, wineberry, whortleberry and the like. Numerous additional and alternative juices suitable for use in at least certain exemplary embodiments will be apparent to those skilled in the art given the benefit of this disclosure. The particular amount of the juice useful for imparting flavor characteristics to the beverages product will depend upon the juice(s) selected, the flavor impression desired, and the form of the juice component. Those skilled in the art, given the benefit of this disclosure, will be readily able to determine the amount of any particular juice(s) used to achieve the desired flavor impression.

Exemplary food products include, but are not limited to any ingredient or any combination of ingredients, or any substance or any combination of substances, that can be used or prepared for use as food for a mammal and includes, but is not limited to, substances that may be used in the preparation of food (such as frying oils) or food additives. As used here and in the appended claims, the term "food ingredients" may include, but are not limited to, acidulants, natural and artificial gums, pharmaceutical preparations, beverages (e.g., soft drinks, carbonated beverages, ready to mix beverages, etc.), infant formula, infused foods (e.g. fruits and vegetables), sauces, condiments, salad dressings, fruit juices, syrups, desserts (e.g., puddings, gelatin, icings and fillings, baked goods and frozen desserts such as ice creams and sherbets), soft frozen products (e.g., soft frozen creams, soft frozen ice creams and yogurts, soft frozen toppings such as dairy or non-dairy whipped toppings), confections, toothpaste, mouthwash, chewing gum, oils and emulsified products (e.g., shortening, margarine, mayonnaise, butter, cooking oil, and salad dressings) and intermediate moisture foods (e.g., rice and dog foods). Furthermore, food ingredients described herein can also be ingested as an additive or supplement contained in foods and drinks. These can optionally be formulated together with a nutritional substance, such as any of various vitamins and minerals. The food ingredients may also optionally be incorporated into substantially liquid compositions, such as, e.g., nutrient drinks, soymilks and soups; substantially solid compositions, and gelatins or used in the form of a powder to be incorporated into various foods.

Those of ordinary skill in the art will understand that, for convenience, some ingredients are described here in certain cases by reference to the original form of the ingredient in which it is added to the sweeteners, solutions, components, products, and compositions disclosed here. Such original form may differ from the form in which the ingredient is found in the finished sweetener, syrup, solution, food or beverage product, component or composition. Thus, for example, sucrose and liquid sucrose would typically be substantially homogenously dissolved and dispersed in a solution. Likewise, other ingredients identified as a solid, concentrate (e.g., juice concentrate), etc. would typically be homogenously dispersed throughout the sweetener, syrup, solution food or beverage product, component, or composition, rather than remaining in their original form. Thus, reference to the form of an ingredient of a sweetener, syrup, solution, food or beverage product, component, or composition should not be taken as a limitation on the form of the ingredient in the sweetener, syrup, solution, food or beverage product, component, or composition, but rather as a convenient means of describing the ingredient as an isolated component of the sweetener, syrup, solution, food or beverage product, component, or composition.

As used here and in the appended claims, the term "under vacuum" or "under sufficient vacuum" is defined as a pressure that is lower than atmospheric pressure, i.e., below about 1 atm (760 torr or 0.1 MPa), preferably below about 0.5 atm. In certain exemplary embodiments disclosed here, heating Reb D under vacuum is accomplished by using a vacuum oven. As used here and in the appended claims, the term "vacuum oven" is defined as an oven where the heat-treating takes place inside a chamber that is airtight, allowing a vacuum to be drawn inside the chamber. The entire heat-treating process can take place under vacuum or precisely controlled atmospheres can be introduced. Vacuum ranges for vacuum ovens can be rough or low (<760, <1 torr), medium (<1, <$10^{-3}$ torr), high vacuum (<$10^{-3}$, <$10^{-8}$ torr), and ultra-high vacuum (<$10^{-8}$ torr).

As used here and in the appended claims, the term "at least a majority of" is defined as including, but not limited to at least 50%, at least 75%, or at least 95%. In certain exemplary embodiments of the methods disclosed here, at least 50% by weight, at least 75% by weight, or at least 95% by weight of the anhydrous compound is converted to anhydrous compound.

As used here and in the appended claims, the term "sufficient temperature" is defined as the temperature necessary to convert at least a majority of the non-anhydrous compound to anhydrous compound. In certain exemplary embodiments disclosed here, suitable temperatures are at least within the temperature range of 80°-110° C., e.g., 100° C.

As used here and in the appended claims, the term "sufficient length of time" is defined as the time necessary to convert at least a majority of the non-anhydrous compound to anhydrous compound. In certain exemplary embodiments disclosed here, a suitable amount of time is from at least 24 hours, from at least 50 hours, from at least 100 hours, and from at least 120 hours.

As used here and in the appended claims, the phrase "non-anhydrous form of the compound includes non-anhydrous Reb D in a dry powder state" is taken to mean that the initial state of the non-anhydrous form of the compound suitable for conversion to the anhydrous form of the compound is in the form of a dry powder.

As used here and in the appended claims, the phrase "dissolving under heat a quantity of the thermally stable anhydrous form of the compound . . . in at least water to form an aqueous solution" is defined as heating by sufficient means before, after, or during the addition of a compound to a solution. It should be understood that as used here and in the appended claims, heating an aqueous solution is taken to mean that the solution is heated to a temperature sufficient to dissolve the anhydrous compound in water without decomposing the compound. In exemplary embodiments of the invention, the aqueous solution is heated to temperatures at least within the temperature range of 50°-100° C. e.g., to at least 60°-90° C., or to at least 70°-80° C. In certain exemplary embodiments of the invention, the aqueous solution is heated to 60° C.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. Although the subject matter has been described in language specific to sweeteners, solutions, components, products, compositions and methodological acts, it is to be understood that the subject matter defined in the appended claims is not necessarily limited to the specific sweeteners, solutions, components, products, compositions or acts described above. Rather, the specific sweeteners, solutions, components, products, compositions, and acts described above are disclosed as example forms of implementing the inventive sweeteners, solutions, components, products, compositions and methods defined by the following claims.

I claim:

1. A thermally stable anhydrous compound of formula:

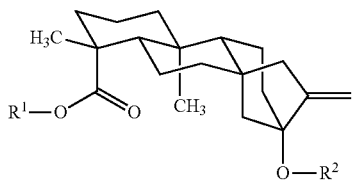

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, and wherein the anhydrous compound is soluble at a concentration greater than 3000 ppm in room temperature water.

2. The thermally stable anhydrous compound according to claim 1, wherein the anhydrous compound is more soluble in water at temperatures at least within the temperature range of 135°-150° F. than a non-anhydrous form of the compound.

3. A sweetener comprising a thermally stable anhydrous compound of formula:

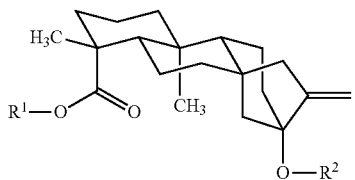

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, and wherein the anhydrous compound is soluble at a concentration greater than 3000 ppm in room temperature water, and wherein the anhydrous compound is at least 50% by weight of the sweetener.

4. The sweetener according to claim 3, wherein the thermally stable anhydrous compound is at least 90% by weight of the sweetener.

5. A supersaturated aqueous solution comprising a thermally stable compound of formula:

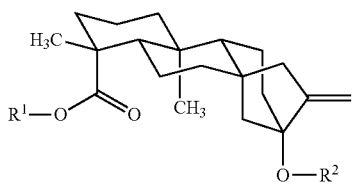

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, and wherein the concentration of the compound in the supersaturated aqueous solution is at least 3000 ppm.

6. A beverage product comprising:

A) a sweetener component comprising a thermally stable anhydrous compound of formula:

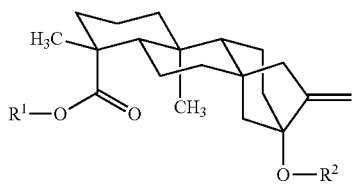

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, and wherein the anhydrous compound is soluble at a concentration greater than 3000 ppm in room temperature water; and B) at least one other beverage ingredient.

7. The beverage product according to claim 6, wherein the thermally stable anhydrous compound is at least 50% by weight of the sweetener component.

8. The beverage product according to claim 7, wherein the concentration of the sweetener component in the beverage product is at least 500 ppm.

9. The beverage product according to claim 6, wherein the at least one other beverage ingredient is an aqueous solution.

10. The beverage product according to claim 6, wherein the beverage product is a carbonated beverage, syrup or a beverage concentrate.

11. The beverage product according to claim 10, wherein the beverage product is a carbonated beverage.

12. The beverage product according to claim 10, wherein the beverage product is a syrup.

13. The beverage product according to claim 10, wherein the beverage product is a beverage concentrate.

14. A beverage product comprising:

an aqueous solution comprising a thermally stable compound of the formula:

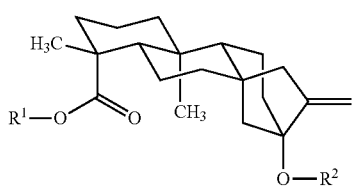

wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, and at least one other beverage ingredient, wherein the compound is soluble at a concentration greater than 3000 ppm in room temperature water, and wherein the compound is at a concentration in the beverage product greater than 500 ppm.

15. A beverage product comprising:
an aqueous solution comprising a thermally stable compound of the formula:
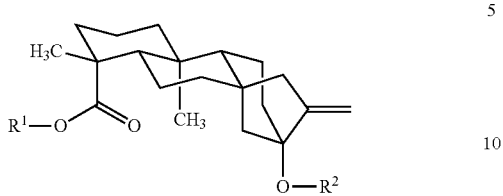
wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl, and
at least one other beverage ingredient,
wherein the compound is at a concentration greater than 3000 ppm in the beverage product.
* * * * *